United States Patent [19]
Fogel

[11] Patent Number: 5,476,648
[45] Date of Patent: Dec. 19, 1995

[54] OIL IN WATER EMULSIONS

[75] Inventor: Arnold W. Fogel, Borough of Upper Saddle River, N.J.

[73] Assignee: Bernel Chemical, Englewood, N.J.

[21] Appl. No.: 31,101

[22] Filed: Mar. 12, 1993

[51] Int. Cl.$^6$ ............................... A61K 7/42; A61K 7/44; A61K 7/48; A61K 9/107

[52] U.S. Cl. ................... 424/59; 424/60; 424/63; 424/65; 514/844; 514/847; 514/873; 514/938

[58] Field of Search ............................. 514/938; 424/59, 424/60, 65

[56] References Cited

U.S. PATENT DOCUMENTS 4,559,226  12/1985  Fogel et al. ............................. 424/66
5,116,604   5/1992  Fogel et al. ............................. 424/59

OTHER PUBLICATIONS

Ele Fac I–205 Suntan Emulsions—Bernel Chemical A New Emulsion Technology—Bernel Chemical AMA Labs, Inc. Summary Sheet—Evaluation of SPF, 1989.

*Primary Examiner*—Dale R. Ore
*Attorney, Agent, or Firm*—Anthony D. Cipollone

[57] ABSTRACT

A novel oil in water emulsion composition comprising of two alkoxylated esters and a neopentanoate ester in varied ratios to produce unique and unexpected properties in formulations. Water thin emulsions, deodorant milk emulsions, dry skin lotion and sunscreen emulsion with high unexpected SPF results are a direct result in the use of this emulsion system in the formulation.

5 Claims, No Drawings

OIL IN WATER EMULSIONS

BACKGROUND OF THE INVENTION

The inventor's initial goal was to discover a water dispersible, self emulsifying surfactant that would be oil soluble and simultaneously have emollient properties with a desirable skin feel. This surfactant when added to $H_2O$ at room temperature would form its own oil in $H_2O$ emulsion and at the same time appear and feel like a cosmetic skin lotion. In addition, the surfactant would be stable, safe and effective at use concentrations.

The result of this effort is U.S. Pat. No. 4,559,226 which introduced at least two self-emulsifying alkoxylated esters having the structural formula:

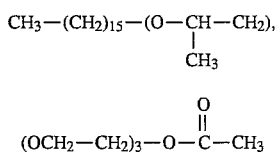

a)

trade name: Hetester® PCA

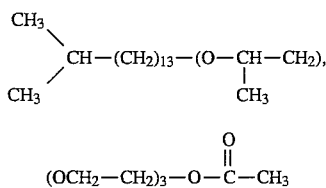

b)

trade name: Hetester® PHA.

Increasing the hydrophilic portion of structure b, to cause water solubility, the resulting compound has the following structure:

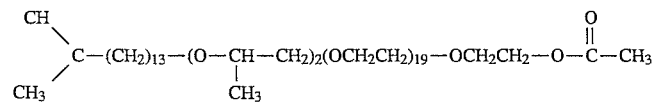

trade name: CUPL® PIC for which Patent Applications have been submitted.

The resulting compound, that is, CUPL® PIC became a fragrance solubilizer and oil in water emulsifier.

The aforementioned Hetesters® proved to be excellent oil in water emulsififers, emulsifying at least twice their own weight in oil. They further proved to be excellent pigment wetters and dispersers.

Both the Hetester® & CUPL® are synthesized and do not contain any animal derived components. They are free of phenolic and oleic groupings. These properties result in non-distortion of fragrances, less tachiness and excellent safety scores.

Recently, U.S. Pat. No. 5,116,604 was issued. The preferred embodiment of this invention has the following structure:

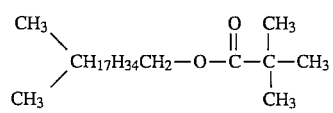

Trade name: Elefac®.

This unique ester was produced by using a specific C-20 alcohol clearly defined in the Patent. The use of this specific C-20 alcohol resulted in a neopentanoate ester with an exclusive extraordinary emolliency that significantly enhances sun protective factor (SPF) of a sunscreen formulation. In addition, it has these desirable properties: clear, low-freezing liquid, good color, odor, non-comedogenic, stable and safe. It is also a moisturizer and pigment wetter for cosmetic products.

Progressing further, various uses of the Hetester® and CUPL® surfactants in combination with the oil soluble ester, Elefac®, gave a water thin, oil in water emulsion without the need for stabilizing water dispersible thickeners. The emulsion thus formed was stable for 3 months at 50° C. and had a perfect freeze/thaw stability.

OBJECTS AND SUMMARY OF THE INVENTION AND DESCRIPTION OF THE INVENTION

It is the object of this invention to introduce a new and novel emulsion system containing a combination of three basic components: 2 surfactants of different hydrophilicity in combination with a unique neopentanoate ester made from a specific alcohol.

Using this combination gives water thin oil in water emulsion without the use of water dispersible gums. The emulsion system alone scored an SPF of 4.35 on 20 people without any active sunscreen present.

It is another object of the instant invention to thicken this "water thin" emollient milk, add Parsol MCX which resulted in the unexpected property of an SPF reading of 13 in 20 people when an SPF of 8 is expected.

Another object of the invention is to make a PABA, PABA derivative, Benzophenone-3, water soluble sunscreen free formula which was accomplished. Using the emulsion system and Parsol MCX and Parsol 1789 resulted in SPF of 17 on 20 people. This result was accomplished without using the forementioned undesirable sunscreens which again, was higher than expected.

Formula F-6-39-1, F-6-46-1, F-7-1-1, and F-7-1-3 are illustrative formulas.

This is the point and thrust of the invention. A unique emulsion system which gives unexpected SPF properties. The unexpected SPF results are additive from the combination of the emulsion system introduced and the sunscreens added.

The goal of any emulsion chemist is to produce a water thin stable oil in H₂O emulsion without the use of any water soluble or dispersable thickeners. The present system introduced in the instant invention brings to fruition this goal. Also an added benefit is the ability to form this emulsion at 38° C.

What is claimed is:

1. A novel oil in water emulsion system used in sunscreen and cosmetic formulations comprising:

a.) an alkoxylated ester having the structural formula:

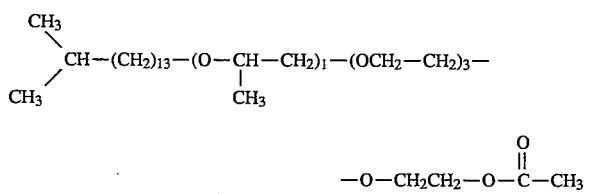

wherein said alkoxylated ester comprises from 3% to 20% and water comprises from 60% to 0.5% weight/weight of the said formulation respectively;

b.) a second alkoxylated ester having the structural formula:

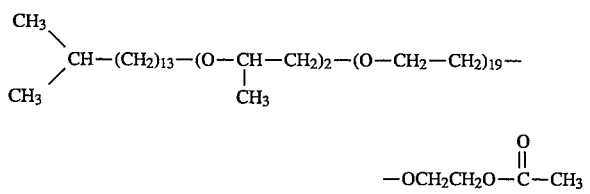

wherein said second alkoxylated ester comprises from 1% to 0.5% weight/weight of the said formulations respectively; and c.) a neopentanoate ester having the structural formula:

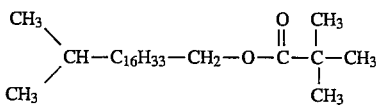

wherein said neopentanoate ester comprises 5% to 25% and water comprises 60% to 85% weight/weight of said formulations respectively.

2. The said water emulsion system of claim 1 wherein the said alboxylated ester having structural formula a.) comprises 7.5%, second alkoxylated ester having structure formula b.) comprises 5.0%, said neopentanoate ester c.) comprises 10.0% and water comprises 77.45% weight/weight of the said formulations.

3. The said oil in water emulsion system of claim 1 wherein the said alkoxylated ester having structural formula a.) comprises of 5.0%, said second alboxylated ester b.) comprises 3.3%, said neopentanoate ester c.) comprises 6.7% and water comprises 84.4 % weight/weight of the said formulation respectively.

4. The said oil in water emulsion of claim 1 wherein the said alboxylated ester having structural formula a.) comprises 7.5%, said second alkoxylated ester having structural formula b.) comprises 5.0%, said neopentanoate ester having structural formula c.) comprises 10.0% and water comprises 69.2% weight/weight of the said formulations respectively.

5. The said oil in water emulsion system of claim 1 wherein the said alkoxylated ester having structural formula a.) comprises 7.5%, said second alboxylated ester having structural formula b.) comprises 5.0%, said neopentanoate ester having structural formula c.) comprises 67.2% weight/weight of the said formulation respectively.

* * * * *